US00PP34595P3

(12) United States Plant Patent
Olesen

(10) Patent No.: US PP34,595 P3
(45) Date of Patent: Sep. 20, 2022

(54) COMPACT FLORIBUNDA ROSE PLANT NAMED 'POULPAL092'

(50) Latin Name: *Rosa hybrida*
Varietal Denomination: 'Poulpal092'

(71) Applicant: Mogens Nyegaard Olesen, Fredensborg (DK)

(72) Inventor: Mogens Nyegaard Olesen, Fredensborg (DK)

(73) Assignee: Poulsen Rose, A/S, Fredensborg (DK)

( * ) Notice: Subject to any disclaimer, the term of this patent is extended or adjusted under 35 U.S.C. 154(b) by 0 days.

(21) Appl. No.: 17/300,624

(22) Filed: Sep. 7, 2021

(65) Prior Publication Data

US 2022/0095513 P1 Mar. 24, 2022

(30) Foreign Application Priority Data

Sep. 21, 2020 (QZ) ..... 2020/2260

(51) Int. Cl.
*A01H 5/02* (2018.01)
*A01H 6/74* (2018.01)

(52) U.S. Cl.
USPC ..... Plt./145
CPC ..... *A01H 6/749* (2018.05)

(58) Field of Classification Search
USPC ..... Plt./143, 145
CPC ..... A01H 5/0222
See application file for complete search history.

(56) References Cited

PUBLICATIONS https://www.poulsenroser.dk/fr/roses/ShowProduct/65810?productGroup=PAL; Oct. 8, 2021; 2 pages.*

* cited by examiner

*Primary Examiner* — Kent L Bell

(57) ABSTRACT

A new garden rose plant of the Compact Floribunda class which has abundant, deep yellow flowers and attractive foliage. This new and distinct variety has shown to be uniform and stable in the resulting generations from asexual propagation.

1 Drawing Sheet

Botanical designation: *Rosa hybrida.*

Variety denomination: 'Poulpal092'.

This application claims priority to Plant Breeder's Rights Application Number 2020/2260, which was filed at the Community Plant Variety Rights Office in the European Union on Sep. 21, 2020, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2012 and the resulting seeds were planted in a controlled environment in Fredensborg, Denmark. The new variety, named 'Poulpal092', originated as a single seedling from the stated cross.

The new variety may be distinguished from its male pollen parent and female seed parent primarily by the following characteristics. The female seed parent plant has a growth height of 60 cm flowers while the new variety has a growth height of 42 cm. The female seed parent has no fragrance in the flowers, while the new variety has a distinct strong perfume in flowers. The male pollen parent plant has near white to pink flowers while the new variety has deep yellow flowers.

The objective of the hybridization of this rose variety was to create a new and distinct variety with unique qualities, such as:

1. Uniform and abundant deep yellow flowers;
2. Vigorous, but compact growth when propagated on its own roots;
3. Exceptional disease resistance.

This combination of qualities is not present in previously available commercial cultivars of this type, known to the inventor, and distinguish 'Poulpal092' from all other varieties of which we are aware.

As part of the rose development program, Mogens N. Olesen germinated the seeds from the aforementioned hybridization during winter of 2012 and conducted evaluations on the resulting seedlings in a controlled environment in Fredensborg, Denmark. 'Poulpal092' was selected in the spring of 2013 by the inventor as a single plant from the progeny of the aforementioned hybridization.

Asexual reproduction of 'Poulpal092' by rooted cuttings was first done by Mogens N. Olesen in the nursery in Fredensborg, Denmark in July, 2013. This initial and other subsequent asexual propagations conducted in controlled environments have demonstrated that the characteristics of 'Poulpal092' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulpal092'. Specifically illustrated in the drawing is an open flower viewed from above, and from the side, petals detached showing reproductive flower parts, sepals detached showing foliaceous appendages and receptacle, leaves, bare stems, and flower buds.

DETAILED DESCRIPTION OF THE VARIETY

The following is a description of 'Poulpal092', as observed in its growth in a controlled environment greenhouse in Odense Denmark. Observed plants are 6 months old and were grown on their own roots in 19 cm containers. Color references are made using The Royal Horticultural Society (London, England) Colour Chart, 2001, except where common terms of color are used.

For a comparison, several physical characteristics of the rose variety 'Poulpal065', U.S. Plant Pat. No. 28,166 are compared to 'Poulpal092' in Chart 1.

CHART 1

| | 'Poulpal092' | 'Poulpal065' |
|---|---|---|
| Petal Count | 42 | 55 |
| Flower Diameter | 57 mm | 90 mm |
| General Tonality of Flower Color | Yellow Orange 15A, becoming Yellow Orange 15D as flowers mature | Yellow Group 6B |
| Flower scent | Very strong perfume | Moderate floral |

Flower and Flower Bud:

Blooming habit: Continuous.

Flower bud:

*Size*.—Upon opening, about 21 mm in length from base of receptacle to end of bud. Bud diameter is 18 mm.

*Bud form*.—Ovoid.

*Bud color*.—As sepals divide petals are Green Yellow Group 1B.

*Sepal inner surface*.—Color: Yellow-Green Group 147A and 147D. Surface: Lightly pubescent.

*Sepal outer surface*.—Color: Yellow-Green Group 146A. Texture: Smooth.

*Sepal shape*.—Generally subulate. Apex: Cirrhose. Base: Flat at union with receptacle.

*Sepal margin*.—Margins have strong foliaceous appendages on three of the five sepals.

*Sepal size*.—About 37 mm long, 15 mm wide.

*Receptacle*.—Texture: Smooth. Size: 5 mm in height, 7 mm wide. Color: Yellow-Green Group 144A. Shape: Funnel.

*Pedicel*.—Surface: Many small prickles and fragrant stipitate glands. Length: About 50 mm. Diameter: 2.5 mm. Color: Yellow-Green Group 144A. Strength: Strong.

*Peduncle*.—Length: About 3 cm. Diameter: 3 mm. Color: Yellow-Green Group 144A. Texture: Smooth.

Flower bud development: Flower buds are borne singly and in clusters of 3 to 5 flower buds per stem.

Flower bloom:

*Fragrance*.—Very strong perfume.

*Duration*.—The blooms have a duration on the plant of approximately 18 days. Petals fall cleanly away from plant after flowers have fully matured.

*Size*.—Flower diameter is 57 mm when open. Flower depth is 35 mm.

*Flower shape*.—Shallow open cup.

*Shape of flower, side view*.—The upper portion is convex. The lower portion is very concave.

Petalage: Under normal conditions, flowers have about 42 petals.

General tonality of flower: Open flowers are Yellow Orange 15A, becoming Yellow Orange 15D as flowers mature.

Petal color:

*Upon opening, outer petals*.—Upper surface: Yellow-Orange Group 21A with basal petal spot Yellow 9A. Lower surface: Yellow Group 12C splashed with Yellow-Orange Group 23C at the middle zone. The basal portion of the petal is Yellow-Orange Group 14B.

*Upon opening, inner petals*.—Upper surface: Yellow-Orange Group 21A. Basal petal spot is Yellow 9A. Lower surface: Yellow Group 12C splashed with Yellow-Orange Group 23C at the middle zone. The basal portion of the petal is Yellow-Orange Group 14B.

*After opening, outer petals*.—Upper surface: Yellow Group 8B with shades of Yellow-Orange Group 16C at the marginal zone. Lower surface: Yellow Group 13A.

*After opening, inner petals*.—Upper surface: Yellow Group 8B with shades of Yellow-Orange Group 16C at the marginal zone. Lower surface: Yellow Group 13A.

Petals:

*Petal reflex*.—Strong.

*Margin*.—Entire and uniform. Moderate undulations.

*Shape*.—Broad and elliptic. Apex shape: Rounded. Base shape: Acute.

*Size*.—26 mm (l)×26 mm (w).

*Texture*.—Smooth.

*Thickness*.—Average.

Petaloids:

*Size*.—10 mm (l) by 10 mm (w).

*Quantity*.—About 8.

*Shape*.—Elliptical to round with an acute base and emarginate apices.

*Color*.—The upper side Yellow-Orange Group 21A with petaloid basal spot Yellow 9A. Lower surface Yellow Group 12C splashed with Yellow-Orange Group 23C at the middle zone, and petaloid spot at the base Yellow-Orange Group 14B.

Reproductive flower parts:

*Pollen*.—None observed.

*Anthers*.—Size: 2 mm in length. Color: Greyed-Orange Group 163A. Quantity: 35 on average.

*Filaments*.—Color: Yellow Group 7A. Length: 6 mm.

*Pistils*.—Length: 9 mm. Quantity: 26 on average.

*Stigmas*.—Color: Greyed-Yellow Group 160A.

*Styles*.—Color: Yellow-Green Group 145C.

*Location of stigmas*.—Superior in location relative to the length of the filaments and the height of the anthers.

*Hips*.—None Observed.

Plant

Plant growth: Upright, bushy, and compact. Plants are about 42 cm in height, and 40 cm wide.

Stems:

*Color of juvenile growth*.—Yellow-Green Group 144B.

*Color of mature growth*.—Yellow-Green Group 144A.

*Length*.—Canes are about 30 cm from the base of the plant to the flowering portion.

*Diameter*.—About 5 mm.

*Internodes*.—22 to 25 mm between nodes.

*Surface texture*.—Young wood: Smooth. Older wood: Smooth.

Long prickles:

*Incidence*.—7 prickles per 10 cm of stem.

*Size*.—Average length of prickles on mature stems is 6 mm.

*Shape*.—Upper portion is linear. Lower portion is linear.

*Color*.—Juvenile prickles: Greyed-Orange Group N170C. Mature prickles: Greyed-Orange Group N170C.

Plant foliage:

*Compound leaf*.—120 mm (l)×80 mm (w).

*Quantity*.—3 or 4 leaves per 10 cm of stem on average.

*Leaf bearing angle to the stem*.—45 degrees.

*Color of juvenile foliage*.—Upper side: Yellow-Green Group 146A with intonations of Greyed-Purple Group N186C. Lower side: Yellow-Green Group 146B with intonations of Greyed-Purple Group 183A.

*Color of mature foliage*.—Upper side: Yellow-Green Group 146A. Lower side: Yellow-Green Group 147B.

Plant leaves and leaflets:

*Stipules*.—Size: 11 mm long, mm wide. Quantity: 2 per compound leaf. Shape: Linear, slightly broad based with outward extending apices. Margins: Lacerate. Color:

Petiole.—Length: 13 mm. Diameter: 2 mm. Upper surface color: Yellow-Green Group 144A. Lower surface color: Yellow-Green Group 144A.

*Rachis*.—Length: 50 mm. Diameter: 1.5 mm. Upper surface color: Yellow-Green Group 144A. Lower surface color: Yellow-Green Group 144A.

*Leaflet*.—Quantity: 5 to 7 leaflets. Juvenile leaves are occassionally trifoliate. Margins: Serrated. Size: Terminal leaflets are about 50 mm long, 36 mm wide. Shape: Generally elliptical. Base: Rounded. Apex: Acute. Texture: Smooth. Thickness: Average. Arrangement: Odd pinnate. Venation: Reticulate. Glossiness: Not glossy.

Disease resistance: Above average resistance to powdery mildew *Sphaerotheca pannosa* var. *Rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

Pest resistance: The variety is susceptible to any insect pest normally associated with the species.

I claim:

1. A new and distinct variety of rose plant of the Compact Floribunda rose class named 'Poulpal092', substantially as illustrated and described herein, due to its abundant deep yellow flowers, disease resistance, and extended period of bloom.

* * * * *

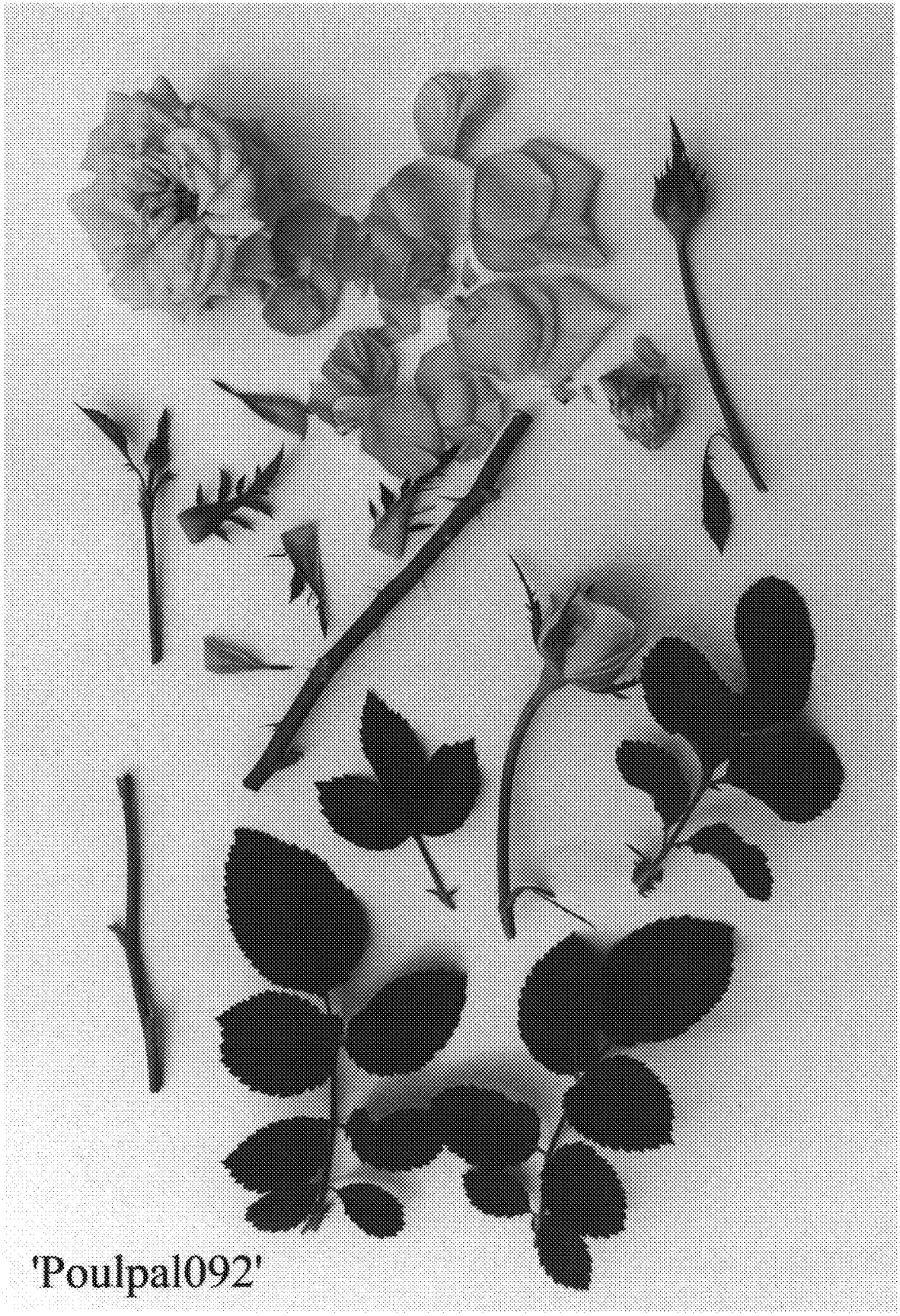
'Poulpal092'